(12) United States Patent
Pugh

(10) Patent No.: US 9,687,540 B2
(45) Date of Patent: Jun. 27, 2017

(54) CROSS-PROTECTING SALMONELLA VACCINES

(71) Applicant: Intervet Inc., Madison, NJ (US)

(72) Inventor: Christopher Pugh, Northampton (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/437,524

(22) PCT Filed: Oct. 25, 2013

(86) PCT No.: PCT/EP2013/072358
§ 371 (c)(1),
(2) Date: Apr. 22, 2015

(87) PCT Pub. No.: WO2014/064236
PCT Pub. Date: May 1, 2014

(65) Prior Publication Data
US 2015/0290310 A1    Oct. 15, 2015

(30) Foreign Application Priority Data
Oct. 26, 2012   (EP) ..................................... 12190173

(51) Int. Cl.
*A61K 39/112* (2006.01)
*A61K 39/39* (2006.01)
*A61K 39/00* (2006.01)

(52) U.S. Cl.
CPC .......... *A61K 39/0275* (2013.01); *A61K 39/39* (2013.01); *A61K 2039/522* (2013.01); *A61K 2039/552* (2013.01); *A61K 2039/55505* (2013.01)

(58) Field of Classification Search
CPC .......... A61K 2039/552; A61K 39/0275; A61K 2039/522; A61K 9/0017; A61K 2039/521; A61K 2039/545; A61K 2039/55505; A61K 2039/70; A61K 39/39; A61K 39/39533; A61K 39/39583
See application file for complete search history.

(56) References Cited

FOREIGN PATENT DOCUMENTS

| EP | 0650733 A1 | 5/1995 |
| JP | 2009-215226 | 9/2009 |
| WO | 2008073891 A2 | 6/2008 |

OTHER PUBLICATIONS

Responsible Use of Medicines in agriculture Alliance (ruma) 2006.*
Deguchi, K. et al, Efficacy of a novel trivalent inactivated vaccine against the shedding of *Salmonella* in a chicken challenge model, Avian Diseases, 2009, pp. 281-286, 53, WO.
Grimont P.A.D. & Weill F., Antigentic formulae of the *Salmonella* serovars, WHO Collaboration Centre for reference and research on *Salmonella*, 2007, pp. 1-166, 9th edition, EP.
Methner U., et al, Exploitation of intestinal colonization-inhibition between *Salmonella* Oganisms for live vaccines in Poultry—potential and limitations, Zoonoses and public health, 2011, pp; 540-548, 58, EP.
Pavic A., The control of poultry *Salmonella* colonisation by vaccination and prophylactic treatment with anti-*Salmonella* antibodies, A thesis submitted to the University of New South Wales as fulfilment of the requirements for the degree of Doctor in Philosophy, Aug. 2010, pp. 144-185, XP055090505, WO.
Pavic, A. et al., Utilization of a novel autologous killed tri-vaccine (serogroups B [Typhimurium], C [Mbandaka] and E [Orion]) for *Salmonella* control in commerical poultry breeders, Avian Pathology, Feb. 2010, pp. 31-39, 39(1), EP.
Dórea, F.C. et al., Effect of *Salmonella* vaccination of breeder chickens on contamination of broiler chicken carcasses in integrated poultry operations, Applied and Environmental Microbiology, Dec. 2010, pp. 7820-7825, vol. 76, No. 23.
Mohler, V.L. et al., Cross-protective immunity conferred by a DNA adenine methylase deficient *Salmonella enterica* serovar Typhimurium vaccine in calves challenged with *Salmonella* serovar Newport, Vaccine, 2008, pp. 1751-1758, 26.
Nichiju, Kaishi, Review of Vaccine for chickens, unknown, 2011, pp. 610-612, vol. 64.
Duffey, P.S., et al., *Salmonella* Serogroups C2 and C3 Identified by Agglutination Using an Immunoglobulin G3(k) Monoclonal Antibody (32-1-E3) Reactive with a Somatic Factor 8-Like Polysaccharide Antigen, Journal of Clinical Microbiology, Dec. 1992, pp. 3050-3057, vol. 30, No. 12.
Smith, B.P., et al., Enzyme-linked immunosorbent assay for *Salmonella* serology using lipopolysaccharide antigen, J. Vet. Diagn. Invest., 1995, pp. 481-487, 7.

* cited by examiner

*Primary Examiner* — Padma V Baskar

(57) ABSTRACT

The present invention discloses that *Salmonella enterica* serogroup C2-3 serovars cross protect against *Salmonella enterica* serogroup C1 serovars and vice versa. Therefore, the present invention discloses the use of either a *Salmonella enterica* serogroup C2-3 serovar or a *Salmonella enterica* serogroup C1 serovar in the manufacture of a vaccine for administration to poultry to protect against a disorder arising from a *Salmonella enterica* serogroup C2-3 serovar and/or a disorder arising from a *Salmonella enterica* serogroup C1 serovar.

2 Claims, 10 Drawing Sheets

CROSS-PROTECTING *SALMONELLA* VACCINES

CROSS-REFERENCE TO RELATED APPLICATIONS

Figure 1:
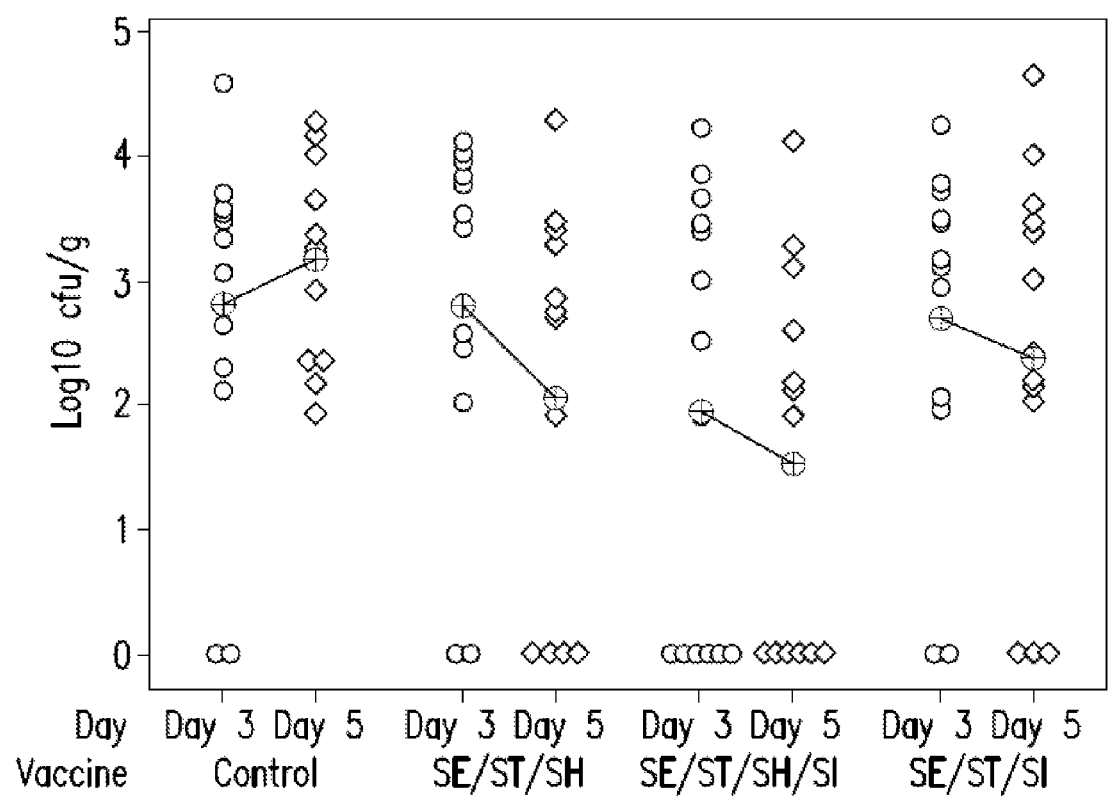
Figure 1:
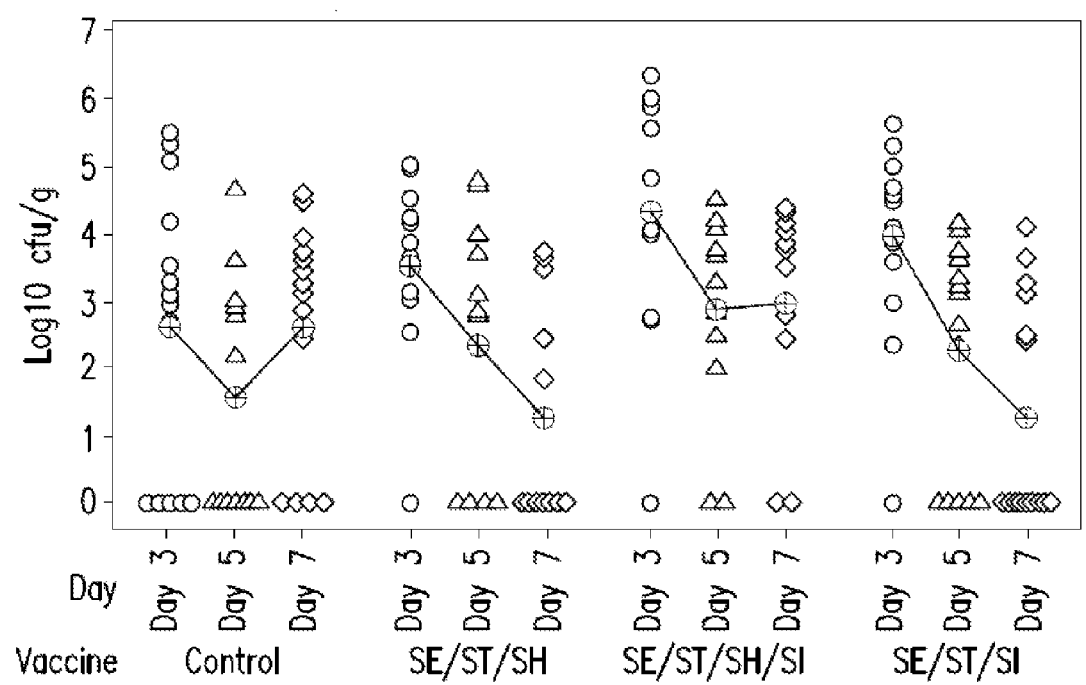
Figure 1:
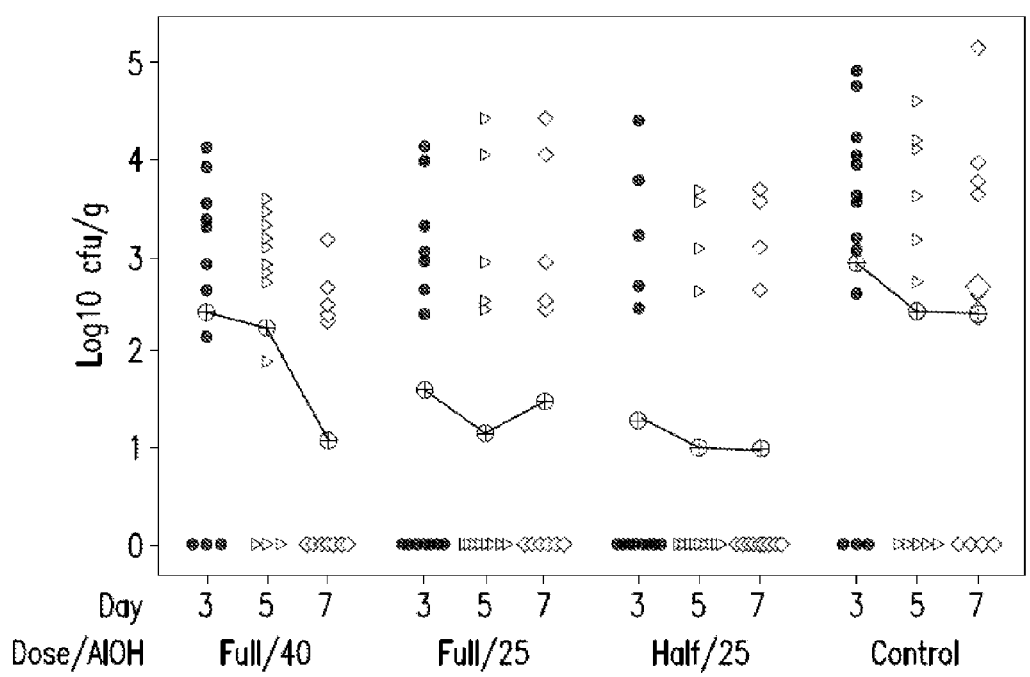

This application is a national stage entry under 35 U.S.C. §371 of PCT/EP2013/072358, filed on Oct. 25, 2013, which claims priority to EP Application No. EP12190173.0, filed on Oct. 26, 2012. The content of PCT/EP2013/072358 is hereby incorporated by reference in its entirety.

FIELD OF THE INVENTION

The present invention pertains to the cross protection of *Salmonella enterica* serogroup C2-3 serovars with *Salmonella enterica* serogroup C1 serovars, allowing the manufacture of vaccines that comprise a serovar from only one of these two distinct serogroups to protect against either *Salmonella enterica* serogroup.

BACKGROUND

*Salmonella* is a major pathogen of poultry, and its presence in poultry flocks is a major concern for human public health. Incidents of food poisoning caused by *Salmonella* remain prevalent throughout the world, and are second only to *Campylobacter* as the most common cause of food poisoning due to bacteria. Not surprisingly, poultry products are a primary source of *Salmonella* infections in humans, with the transfer of this pathogen originating either from laying hens to eggs, or from broiler carcasses to meat products. *Salmonella Enteritidis* (SE) is especially important in egg-associated food poisoning due to the ability of some strains to colonize the reproductive tissues of hens, which can result in the presence of live *Salmonella* in the eggs and/or on the egg shell.

Contamination by *Salmonella* can be controlled to an extent through the use of effective biosecurity measures, competitive exclusion products, and disinfection procedures. These measures are used in conjunction with vaccination to provide the optimum protection against a poultry flock becoming contaminated, with vaccination being an effective aid in reducing the contamination of eggs by SE. Indeed, since the introduction of vaccines in *Salmonella* control programs in the 1990's, their use has become widespread throughout many parts of the world.

The inactivated vaccines NOBILIS SALENVAC® and SALENVAC T®, which were introduced first, have been almost entirely replaced in the egg producer market by live vaccines, due to the early protection afforded and reduced cost, particularly in labour, as administration can be accomplished through the drinking water. Thus within the egg producing portion of the poultry industry, vaccination with a live *Salmonella* vaccine during the first week of life has become standard practice in the United Kingdom and is becoming more common throughout the European Union. Whereas repeated vaccination is claimed to offer protection of the hens throughout the flock life, many producers follow an initial live vaccination program with a dose or course of an inactivated vaccine. The basis of this latter procedure is that antibodies present in the yolks of eggs laid by hens that had been vaccinated with an inactivated vaccine have been shown to reduce the growth of *Salmonella* compared to those from either unvaccinated hens or hens vaccinated with a live vaccine. Inactivated vaccines also remain common practice in the poultry meat industry, as they provide passive protection to newly hatched chicks against *Salmonella* via transfer of antibodies through the egg [Inoue et al. *Avian Diseases* 52:567-571 (2008)].

*Salmonella* spp. is a Gram-negative bacterial genus that is divided into two species, *S. enterica* and *S. bongori*. *S. enterica* contains 6 major serogroups (A, B, C1, C2-3, D, and E) that have been classified according to their lipopolysaccharide structure. Essentially all existing vaccines on the market claim to protect against *Salmonellae* of serogroups B (i.e., serovar *S. Typhimurium*) and D (i.e., serovar *S. Enteritidis*) and thereby, specifically target the reduction of these serovars. Indeed, until recently, these serogroups were not only the most prevalent, but also the most important from a zoonotic viewpoint. However, though *S. Enteritidis* and *S. Typhimurium* are still the most common serovars involved in human disease in Europe, their prevalence in contaminated chicken products appears to be declining, whereas *Salmonellae* of the serogroups C1 (which includes e.g., *S. Infantis, S. Mbandaka*, and *S. Virchow*) and C2-3 (which includes, e.g., *S. Hadar, S. Newport* and *S. Kentucky*) have significantly increased in prevalence. Notably, a vaccine that comprises serovars *S. Typhimurium* (serogroup B) and *S. Enteritidis* (serogroup D) has been shown to provide cross-protection against other serovars of serogroup B, i.e., *S. Heidelberg* and *S. Agona*, but failed to show any efficacy against a challenge with *S. Hadar* (serogroup C2-3), indicating a need for additional antigens in vaccines to provide the necessary protection.

More recently, an inactivated trivalent vaccine containing *S. Enteritidis* (serogroup D), *S. Typhimurium* (serogroup B), and *S. Infantis* (serogroup C1), has been reported to be efficacious against a challenge from *S. Enteritidis, S. Typhimurium, S. Infantis*, or *S. Heidelberg* (serogroup B) [Deguchi et al., *Avian Disease* 53:281-286 (2009)]. In addition, another inactivated trivalent vaccine containing *S. Typhimurium* (serogroup B), *S. Mbandaka* (serogroup C1) and S. Orion (serogroup E) also has been reported to protect against several serogroup B and C1 serovars, though the results with the serogroup E serovars were inconclusive [Pavic et al., *Avian Pathology* 39 (1):31-39 (2010)].

The O antigen is a major lipopolysaccharide component of the cell surface of all Gram-negative bacteria. Each of the serogroups of *S. enterica* express distinguishable O antigens and accordingly, the O antigen can be used in their classification [Nori and Thong, *African Journal of Microbiology Research* 4(9) 871-876 (2010)]. Consistently, little to no cross-reaction was found between the six different *S. enterica* serogroups when an enzyme-linked immunosorbent assay was performed (ELISA) [Smith et al., *J. Vet. Diagn. Invest.*, 7:481-487 (1995)].

The O antigen is encoded by multiple genes in the rib gene cluster of the *S. enterica* genome and not surprisingly, there are significant differences within the rfb gene clusters between the 6 major serogroups of *S. enterica* [Lee et al., *J. Gen. Microbiol.*, 138:1843-1855 (1992); Nori and Thong, *African Journal of Microbiology Research* 4(9) 871-876 (2010)]. More particularly, the rfb gene cluster of serogroup C1 has been shown to have only limited similarity to the rfb cluster of serogroups A, B, C2-3, D, or E [Lee et al., *J. Gen. Microbiol.*, 138:1843-1855 (1992)]. Furthermore, a monoclonal antibody raised against a heated alcohol-acetone-extracted serogroup C2-3 serovar (S. Newport) reacted with protein-free lipopolysaccharides from other serogroup C2-3 serovars, but not with protein-free lipopolysaccharides from any other serogroup. In addition, the reactivity with this monoclonal antibody was inhibited by preincubation of the corresponding antigen from serogroup C2-3 with polyclonal rabbit anti-serogroup C2-C3 antibodies, but not by preincubation of that antigen with polyclonal antisera obtained from serogroup C1 antigen, or any other *Salmonella* serogroup antigen tested [Duffey et al., *J. Clin. Microbiol.* 30(12): 3050-3057 (1992)].

Although vaccines against specific *Salmonella* serogroups have been commercially available for several decades, there remains a need to provide *Salmonella* vaccines that can protect against both *Salmonella* serogroups C1 and C2-3, as well as against serogroups B and D.

The citation of any reference herein should not be construed as an admission that such reference is available as "prior art" to the instant application.

SUMMARY OF THE INVENTION

In order to overcome the deficiencies of current vaccines against *Salmonella*, one aspect of the present invention provides a *Salmonella enterica* serogroup C1 serovar for use in protecting poultry against a disorder arising from *Salmonella enterica* serogroup C2-3 infection, or *Salmonella enterica* serogroup C2-3 and *Salmonella enterica* serogroup C1 infection. Analogously, the present invention provides for the use of a *Salmonella enterica* serogroup C1 serovar in the manufacture of a vaccine for administration to poultry to protect against a disorder arising from *Salmonella enterica* serogroup C2-3 infection, or *Salmonella enterica* serogroup C2-3 and *Salmonella enterica* serogroup C1 infection. In specific embodiments the *Salmonella enterica* C1 vaccine is for administration to chickens.

In a particular embodiment the *Salmonella enterica* serogroup C1 serovar is *S. Livingstone*. In another embodiment the *Salmonella enterica* serogroup C1 serovar is *S. Mbandaka*. In yet another embodiment the *Salmonella enterica* serogroup C1 serovar is *S. Montevideo*. In still another embodiment the *Salmonella enterica* serogroup C1 serovar is *S. Ohio*. In yet another embodiment the *Salmonella enterica* serogroup C1 serovar is *S. Thompson*. In still another embodiment the *Salmonella enterica* serogroup C1 serovar is *S. Virchow*. In a specific embodiment the *Salmonella enterica* serogroup C1 serovar is *S. Infantis*.

In another aspect, the present invention provides a *Salmonella enterica* serogroup C2-3 serovar for use in protecting poultry against a disorder arising from *Salmonella enterica* serogroup C1 infection, or *Salmonella enterica* serogroup C2-3 and *Salmonella enterica* serogroup C1 infection. Analogously, the present invention provides for the use of a *Salmonella enterica* serogroup C2-3 serovar in the manufacture of a vaccine for administration to poultry to protect against a disorder arising from *Salmonella enterica* serogroup C1 infection, or *Salmonella enterica* serogroup C2-3 and *Salmonella enterica* serogroup C1 infection. In specific embodiments the *Salmonella enterica* C2-C3/vaccine is for administration to chickens.

In a particular embodiment the *Salmonella enterica* serogroup C2-3 serovar is *S. Blockley*. In another embodiment the *Salmonella enterica* serogroup C2-3 serovar is *S. Bovismorbificans*. In yet another embodiment the *Salmonella enterica* serogroup C2-3 serovar is *S. Kentucky*. In still another embodiment the *Salmonella enterica* serogroup C2-3 serovar is *S. Kottbus*. In yet another embodiment the *Salmonella enterica* serogroup C2-3 serovar is *S. Muenchen*. In still another embodiment the *Salmonella enterica* serogroup C2-3 serovar is *S. Newport*. In a specific embodiment the *Salmonella enterica* serogroup C2-3 serovar is *S. Hadar.*

The present invention also provides the *Salmonella enterica* serogroup C1 serovar or a *Salmonella enterica* serogroup C2-3 serovar in combination with a *Salmonella enterica* serogroup B serovar for additional protection of poultry against a disorder arising from a *Salmonella enterica* serogroup B infection. Analogously the present invention further provides for the use of a *Salmonella enterica* serogroup C2-3 serovar or a *Salmonella enterica* serogroup C1 serovar in the manufacture of a vaccine of the present invention that further includes the use of a *Salmonella enterica* serogroup B serovar. In a specific embodiment the *Salmonella enterica* serogroup B serovar is *S. Typhimurium*. In other embodiments the *Salmonella enterica* serogroup B serovar can be *S. Agama, S. Agona, S. Derby, S. Heidelberg, S. Indiana, S. Saintpaul, S. Sarajane,* or *S. Monophasic Typhimurium.*

The present invention also provides the *Salmonella enterica* serogroup C1 serovar or a *Salmonella enterica* serogroup C2-3 serovar in combination with a *Salmonella enterica* serogroup D serovar for additional protection of poultry against a disorder arising from a *Salmonella enterica* serogroup D infection. Analogously the present invention further provides for the use of a *Salmonella enterica* serogroup C2-3 serovar or a *Salmonella enterica* serogroup C1 serovar in the manufacture of a vaccine of the present invention that further includes the use of a *Salmonella enterica* serogroup D serovar. In a specific embodiment the *Salmonella enterica* serogroup D serovar is *Salmonella Enteritidis*. In another such embodiment, the *Salmonella enterica* serogroup D serovar is *S. Pullorum/Gallinarum.*

The present invention also provides the *Salmonella enterica* serogroup C1 serovar or a *Salmonella enterica* serogroup C2-3 serovar in combination with a *Salmonella enterica* serogroup B serovar and a *Salmonella enterica* serogroup D serovar for additional protection of poultry against a disorder arising from a *Salmonella enterica* serogroup B and *Salmonella enterica* serogroup D infection. Analogously, the present invention also provides for the use of a *Salmonella enterica* serogroup C2-3 serovar or a *Salmonella enterica* serogroup C1 serovar in the manufacture of a vaccine of the present invention that further includes the use of a *Salmonella enterica* serogroup B serovar and a *Salmonella enterica* serogroup D serovar. In a specific embodiment of this type, the present invention provides for the use of *Salmonella enterica* serovars *Enteritidis, Typhimurium* and *Infantis*, including in the manufacture of a vaccine, for protection of poultry against a disorder arising from a *Salmonella enterica* serogroup C1, C2-C3, B, and D infection. In another such embodiment, the present invention provides for the use of *Salmonella enterica* serovars *Enteritidis, Typhimurium* and *Hadar*, including in the manufacture of a vaccine, for protection of poultry against a disorder arising from a *Salmonella enterica* serogroup C1, C2-C3, B, and D infection.

The present invention further provides for the use of a *Salmonella enterica* serogroup C2-3 serovar or a *Salmonella enterica* serogroup C1 serovar of the present invention, including in the manufacture of a vaccine, that further includes the use of a *Salmonella enterica* serogroup G serovar (e.g., *S. Durham, S. Kedougou, S. Mishmarhaemek,* or *S. Poona*), a *Salmonella enterica* serogroup E1 serovar (e.g., *S. Anatum, S. Binza, S. Orion,* or *S. Thomasville*), or a *Salmonella enterica* serogroup E4 serovar (e.g., *S. Senftenberg*).

All of the *Salmonella enterica* serovars used by the present invention, including those in the manufacture of vaccines, can be grown in iron-restricted medium, resulting in iron-restricted cells. In certain embodiments, the *Salmonella enterica* serovars are inactivated. In a particular embodiment of the present invention the *Salmonella enterica* serovars and/or corresponding vaccine manufactured, is a liquid suspension of formalin-killed, iron-restricted cells of *Salmonella enterica* serovars *Enteritidis, Typhimurium*, and *Infantis*. In another embodiment of the present invention the *Salmonella enterica* serovars and/or corresponding vaccine manufactured, is a liquid suspension of formalin-killed, iron-restricted cells of *Salmonella enterica* serovars *Enteritidis, Typhimurium*, and *Hadar*. In certain embodiments the *Salmonella enterica* serovars are live. In specific embodiments the live *Salmonella enterica* serovars are attenuated.

The present invention further provides for *Salmonella enterica* serovars, and/or corresponding manufacture of vaccines, comprising formalin-killed, iron-restricted cells of *Salmonella enterica* serovars *Enteritidis, Typhimurium*, and either *Infantis* or *Hadar* that further include the use of avian rhinotracheitis, one or more strains of infectious bronchitis virus, Newcastle disease virus, and egg drop syndrome virus. In alternative embodiments, the present invention further provides for *Salmonella enterica* serovars, and/or corresponding manufacture of vaccines, comprising formalin-killed, iron-restricted cells of *Salmonella enterica* serovars *Enteritidis, Typhimurium*, and either *Infantis* or *Hadar* that further include the use of avian rhinotracheitis, one or more strains of infectious bronchitis virus, Newcastle disease virus, and infectious bursal disease virus (Gumboro disease), and inactivated Reovirus. In still other embodiments, the present invention further provides for *Salmonella enterica* serovars, and/or corresponding manufacture of vaccines, comprising formalin-killed, iron-restricted cells of *Salmonella enterica* serovars *Enteritidis, Typhimurium*, and either *Infantis* or *Hadar* that further include the use of inactivated Reovirus, one or more strains of infectious bronchitis virus, infectious bursal disease virus (Gumboro disease), and a *C. perfringens* alpha toxoid.

All of the *Salmonella enterica* serovars of the present invention, and/or corresponding vaccines manufactured through the use of the *Salmonella enterica* serogroups, can be administered either once, or by a first (e.g., primary) vaccination that is followed by a second (booster) and/or additional booster vaccinations. As mentioned above, inactivated *Salmonella enterica* serovars of the present invention, and/or a corresponding vaccine manufactured through the use of the inactivated *Salmonella enterica* serogroups, also can be administered subsequent to an earlier live *Salmonella enterica* vaccination of the poultry subject.

These and other aspects of the present invention will be better appreciated by reference to the following Figures and the Detailed Description.

BRIEF DESCRIPTION OF THE DRAWINGS

FIGS. 1A-1C compare the efficacy of trivalent and/or quadruvalent serovar vaccines and a control with respect to the number of days following a challenge with *S. Hadar*. The data is presented as individual points for each bird. The efficacy is reflected by the $\log_{10}$ cfu/g of the challenge serovar that was isolated by cloacal swabs. FIGS. 1A and 1B compare the efficacy of the two trivalent vaccines (SE/ST/SI and SE/ST/SH) and a quadruvalent vaccine (Quad 1, SE/ST/SH/SI) versus a control.

FIG. 1A (Study 1 *Hadar* challenge: Individual bird cloacal swab) depicts the data obtained in Study 1 at Day 3 (●) and Day 5 (♦) post challenge, whereas FIG. 1B (Study 2 *Hadar*: Cloacal swabs individual birds) depicts the data obtained in Study 2 at Days 3 (●), 5 (▲), and 7 (♦) post challenge.

FIG. 1C (Study 3: Individual bird shedding vs. time. *Hadar* challenge) depicts the data obtained at Days 3 (●), 5 (▲), and 7 (♦) from Study 3, which compares the efficacy of three different quadruvalent (SE/ST/SH/SI) formulations versus a control.

Table 1 below, provides the contents of each of the vaccines tested. The mean values are depicted (⌖) in FIGS. 1A-1C.

FIGS. 2A-2B depict the percentage of birds positive by direct culture, as determined with post-mortem organ isolations obtained on Day 7 following an *S. Hadar* challenge.

FIG. 2A (Study 1 *Hadar*: Proportion of birds positive by direct culture (day 7)) shows the results from Study 1, as described in FIG. 1A, comparing post mortem samples from the caecum, liver, and spleen.

FIG. 2B (Study 2 *Hadar*: Proportion of birds positive by direct culture (day 7)) shows the results from Study 2, as described in FIG. 1B, comparing post mortem samples from the caecum and spleen.

Legend: ▩ SE/ST/SH ▨ SE/ST/SI ▦ SE/ST/SH/SI □ Control

Table 1 below, provides the contents of each of the vaccines tested.

FIGS. 3A-3C depict the percentage of birds positive by direct culture, as determined with post-mortem organ isolations obtained on Day 7 and/or Day 14 following an *S. Infantis* challenge. Studies 1 and 2 compare two trivalent vaccines (SE/ST/SI and SE/ST/SH), and one quadruvalent vaccine (Quad 1, as defined below) versus a control.

FIG. 3A (Study 1 *Infantis*: Proportion of direct positive samples day 7) shows the comparison of post mortem caecum samples at Day 7 for Study 1.

FIG. 3B (Study 1 *Infantis*: Proportion of direct positive spleen samples day 14) shows the comparison of post mortem spleen samples at Day 14 for Study 1.

FIG. 3C (Study 2 *Infantis*: Proportion of direct positive samples at day 7) shows the comparison of post mortem liver and spleen samples at Day 7 for Study 2. Table 1 below, provides the contents of each of the vaccines tested. The correlation of the contents of the vaccine and the shading of the bar graph is as provided in FIGS. 2A-2B above.

FIG. 4 depicts the shedding results of Example 3, of challenge bacteria *S. Hadar* in mean Log 10 cfu/g that were recovered from cloacal samples, by direct culture at all sampling dates, for both test groups.

FIG. 5 presents the dissemination results of Example 3, in percentage of total positive spleen samples (by direct and by enrichment culture) for both test groups, at 10 and 14 days post challenge.

DETAILED DESCRIPTION OF THE INVENTION

The present invention discloses that despite the significant antigenic differences previously reported between *Salmonella* serovars from groups C1 and C2-3 as discussed above, the amount of cross protection between these two distinct serogroups is sufficient to allow a vaccine comprising a serovar from either serogroup to protect against serovars from both serogroups. More particularly, the protective capacity of antigens produced from either serogroup C2-3 or C1 serovars have been shown to protect against a challenge by both *S. Hadar* (C2/3) and *S. Infantis* (C1).

Accordingly, the present invention presents data that indicate that a trivalent *Salmonella* vaccine comprising *Salmonella* serovars from serogroups B, D, and in addition, C2-3 or C1, will provide adequate protection across serogroups B and D, as well as C2-3, and C1. The advantages of such a trivalent vaccine over a quadruvalent vaccine include minimizing the cost of goods and minimizing the likelihood of interference of one antigen over another.

In one aspect of the present invention the *Salmonella enterica* serovars are grown in iron restricted medium. The incorporation of an iron chelator in the growth medium of the *Salmonella* serovars induces the bacteria to activate their iron sequestering mechanisms which results in a physiology more closely aligned to growth in vivo than more conventionally grown organisms. This process of growing iron restricted *Salmonella* leads to the production of antibodies to antigens seen during infection and colonization in the field, and thus provide a more effective immune response.

In a specific embodiment, a trivalent vaccine of the present invention can be for reduction of *S. Enteritidis, Typhimurium, Hadar,* and *Infantis* infection or excretion or horizontal transmission or internal organ invasion during rearing and lay, for hens used for egg production, i.e., layers. In another specific embodiment, a trivalent vaccine of the present invention can be for reduction of *S. Enteritidis, Typhimurium, Hadar,* and *Infantis* infection or excretion or horizontal transmission or internal organ invasion during first weeks of life of progeny by passive protection, for use in poultry used in breeding poultry for meat, i.e., broilers and/or roasters.

The use of singular terms for convenience in the description is in no way intended to be so limiting. Thus, for example, reference to a "serovar" includes reference to one or more of such serovars, unless otherwise specified. The use of plural terms is also not intended to be limiting, unless otherwise specified.

The term "approximately" is used interchangeably with the term "about" and signifies that a value is within fifty percent of the indicated value i.e., a dose containing "about" $2 \times 10^9$ cells/ml can contain between 1 and $3 \times 10^9$ cells/ml.

As used herein, a "vaccine" is a composition that is suitable for application to an animal (including, in certain embodiments, humans, while for other embodiments being specifically not for humans) which upon administration to the animal, e.g., chicken, induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines. Accordingly, a trivalent vaccine exemplified below comprises formalin killed, iron restricted cells of *Salmonella enterica* serovars *Enteritidis, Typhimurium,* and *Infantis*.

As used herein, a "multivalent vaccine" is a vaccine that comprises two or more different antigens. In a particular embodiment of this type, the multivalent vaccine stimulates the immune system of the recipient against two or more different pathogens.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, the term "therapeutically effective amount" is an amount of a given antigen, e.g., killed *Salmonella* isolate, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

As used herein, an "adjuvant" is a substance that is able to favour or amplify the cascade of immunological events, ultimately leading to a better immunological response, i.e., the integrated bodily response to an antigen. An adjuvant is in general not required for the immunological response to occur, but favours or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein the term "poultry" can include chickens, turkeys, ducks, geese, quail, and pheasants.

Vaccines:

The present invention provides vaccines that contain either a member of the *Salmonella enterica* serogroup C1 or *Salmonella enterica* serogroup C2-3 that provide sufficient protection against serovars from both serogroups. In a particular embodiment of the present invention the vaccine is a liquid suspension of killed (e.g., with formalin or heat-inactivation) iron-restricted cells of *Salmonella enterica* serovars *Enteritidis, Typhimurium,* and *Infantis*. In a more particular embodiment, the killed *Salmonella enterica* serovars are killed with formalin. In one such embodiment the final concentration of each antigen is about $2 \times 10^9$ cells/ml. In another embodiment, the vaccine comprises aluminium hydroxide adjuvant at about 25% v/v. In a related embodiment the vaccine is administered intramuscularly. In another related embodiment the vaccine is administered to poultry (e.g., chickens) at the minimum age of six weeks.

The present invention further provides for the use of a *Salmonella enterica* serogroup C2-3 serovar or a *Salmonella enterica* serogroup C1 serovar and optionally a *Salmonella enterica* serogroup B serovar and/or *Salmonella enterica* serogroup D serovar in the manufacture of a vaccine of the present invention that further includes the use of one or more strains of avian rhinotracheitis, infectious bronchitis virus, Newcastle disease virus, infectious bursal disease (Gumboro disease), egg drop syndrome virus, Reovirus, and a *Clostridial perfringens* (*C. perfringens*) antigen. In particular embodiments, the *C. perfringens* antigen is a *C. perfringens* alpha toxoid [see, WO2006/113722; US 2006/0233825 A1, the contents of which are hereby incorporated by reference in their entireties]. In other such embodiments, the *C. perfringens* antigen is a recombinant attenuated *C. perfringens* organism [see, U.S. Pat. No. 7,732,187 B2, the contents of which are hereby incorporated by reference in their entireties]. In yet other embodiments the *C. perfringens* antigen is a substantially nontoxic mutein of the *C. perfringens* alpha toxin [see, U.S. Pat. No. 7,972,604 B2, the contents of which are hereby incorporated by reference in their entireties].

The present invention also provides for the use of a *Salmonella enterica* serogroup C2-3 serovar or a *Salmonella enterica* serogroup C1 serovar in the manufacture of a vaccine of the present invention that further includes the use of one or more strains of avian rhinotracheitis, infectious bronchitis virus, Newcastle disease virus, and egg drop syndrome virus. Such vaccines may be particularly directed for egg-producing hens (i.e., layers).

In alternative embodiments, the present invention provides for the use of a *Salmonella enterica* serogroup C2-3 serovar or a *Salmonella enterica* serogroup C1 serovar in the manufacture of a vaccine of the present invention that further includes the use of avian rhinotracheitis, one or more strains of infectious bronchitis virus, Newcastle disease virus, and infectious bursal disease virus (Gumboro disease), and inactivated Reovirus. In alternative embodiments, the present invention provides for the use of a *Salmonella enterica* serogroup C2-3 serovar or a *Salmonella enterica* serogroup C1 serovar in the manufacture of a vaccine of the present invention that further includes the use of inactivated Reovirus, one or more strains of infectious bronchitis virus, infectious bursal disease virus (Gumboro disease), and a *C. perfringens* antigen, e.g., a *C. perfringens* alpha toxoid. Such vaccines may be particularly directed for poultry used in the meat business (i.e., broilers and roasters).

The present invention further provides for the manufacture of vaccines comprising formalin-killed, iron-restricted cells of *Salmonella enterica* serovars *Enteritidis, Typhimurium*, and either *Infantis* or *Hadar* that in addition include the use of avian rhinotracheitis, one or more strains of infectious bronchitis virus, Newcastle disease virus, infectious bursal disease (Gumboro disease), egg drop syndrome virus, Reovirus, and a *Clostridial perfringens* antigen.

Vaccines and immunogenic compositions of the present invention can, but do not necessarily include, physiologically compatible buffers and saline and the like, as well as pharmaceutically acceptable adjuvants. In certain embodiments of the present invention, the vaccines and/or immunogenic compositions of the present invention are stored frozen and accordingly, comprise a cryopreservative, such as dimethyl sulfoxide (DMSO), to preserve the frozen infected cells.

It is also contemplated that the vaccine may be freeze-dried (lyophilized), or otherwise reduced in liquid volume, for storage, and then reconstituted in a liquid diluent before or at the time of administration. Such reconstitution may be achieved using, for example, vaccine-grade water. In certain embodiments, a lyophilized portion of a multivalent vaccine can comprise one or more antigens and the diluent can comprise one or more antigens.

In particular embodiments a vaccine of the present invention (or a portion thereof) can be in a freeze-dried form, e.g., as tablets and/or spheres that are produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres. Such freeze-dried forms can be readily dissolved in a diluent, to enable systemic administration of the vaccine.

Vaccine Administration:

The vaccines and/or immunogenic compositions of the present invention of the present invention may be administered by any conventional means, for example, by systemic administration, including by parenteral administration such as, without limitation, intramuscular or subcutaneous administration, intravenous injection, intradermal injection, in ovo, or by combinations thereof. The vaccines of the present invention also may be administered by mucosal administration, such as by intranasal, intratracheal, rectal, and/or ocular administration. Alternatively, the vaccines may be administered via a skin patch, scarification, or topical administration. It is contemplated that a vaccine of the present invention also may be administered by oral administration, including via the drinking water and/or food of the recipient.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

The immunogenicity level may be determined experimentally by challenge dose titration study techniques generally known in the art. Such techniques typically include vaccinating a number of animal subjects with the vaccine at different dosages and then challenging the animal subjects with the appropriate virulent *Salmonella enterica* serovar to determine the minimum protective dose.

Dose/Administration Interval:

In particular embodiments, two 0.5 ml doses of a vaccine of the present invention are given at least four weeks apart. In particular embodiments the minimum age of first vaccination is 6 weeks, and the second dose should be given at least 3 to 4 weeks before lay.

Other factors affecting the preferred dosage regimen may include, for example, the age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means. It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The present invention may be better understood by reference to the following non-limiting Examples, which is provided as exemplary of the invention. The following Examples are presented in order to more fully illustrate embodiments of the invention. They should in no way be construed, however, as limiting the broad scope of the invention.

EXAMPLES

Example 1

Comparison of Vaccines Containing Different *Salmonella* Serovars

Vaccines were prepared containing inactivated serovars of *Salmonella Enteritidis* (*S. Enteritidis*; SE) and *Salmonella Typhimurium* (*S. Typhimurium*; ST) (NB: The *S. Enteritidis* and *S. Typhimurium* serovars were the same as those in SALENVAC T) alone, or in combination with inactivated serovars of *Salmonella Hadar* (*S. Hadar*; SH) and/or *Salmonella Infantis* (*S. Infantis*; SI). All of the serovars had been grown in iron restricted medium and were formalin inactivated prior to use. The formulations of the vaccines used in the studies are listed in Table 1.

TABLE 1

Vaccine compositions

| Vaccine | S. Enteritidis cells/ml | S. Typhimurium cells/ml | S. Infantis cells/ml | S. Hadar cells/ml | Aluminium hydroxide |
|---|---|---|---|---|---|
| SE/ST | $2 \times 10^9$ | $2 \times 10^9$ | | | 25% |
| SE/ST/SI | $2 \times 10^9$ | $2 \times 10^9$ | $2 \times 10^9$ | | 25% |
| SE/ST/SH | $2 \times 10^9$ | $2 \times 10^9$ | | $2 \times 10^9$ | 25% |
| Quad 1 | $2 \times 10^9$ | $2 \times 10^9$ | $2 \times 10^9$ | $2 \times 10^9$ | 40% |
| Quad 2 | $2 \times 10^9$ | $2 \times 10^9$ | $2 \times 10^9$ | $2 \times 10^9$ | 25% |
| Quad 3 | $1 \times 10^9$ | $1 \times 10^9$ | $1 \times 10^9$ | $1 \times 10^9$ | 25% |

The SE/ST/SH/SI quadruvalent vaccine 1 (Quad 1) contained an additional quantity of adjuvant, because previous studies with analogous vaccines containing a high cell number had suggested that a 25% aluminium hydroxide content might be inadequate for a vaccine containing $8 \times 10^9$ cells/ml in total. The SE/ST/SH/SI quadruvalent vaccine 2 (Quad 2) contained 25% adjuvant to investigate the adjuvant concentration hypothesis, and the SE/ST/SH/SI quadruvalent vaccine 3 (Quad 3) contained a half dose of all antigens to provide a vaccine that had the same total cell concentration as is in the commercially available SALENVAC T (SE/ST).

Two studies (Study 1 and Study 2) compared the efficacy of the two individual trivalent vaccines (SE/ST/SI and SE/ST/SH) with Quad 1, and included a control. A third study, (Study 3) compared the three quadruvalent formulations against a challenge with either *S. Infantis* or *S. Hadar* and included the appropriate controls. The efficacy of the vaccines was tested using a layer breed of chickens from a commercial supplier. The birds were given two intra-muscular vaccinations three weeks apart and challenged three weeks later with an oral dose of approximately $10^{10}$ cfu of either *S. Hadar* or *S. Infantis*.

The samples were processed as follows: The weighed sample was homogenized in sterile buffered peptone water (BPW). The lumps were allowed to settle and an aliquot of the supernatant was serially diluted in sterile BPW. Aliquots of the supernatant and the dilutions were used to inoculate *Salmonella*-selective agar plates. A second aliquot of the supernatant was used to inoculate a bottle of Rappaport Vassiliadis broth which is a selective medium for *Salmonella* [see, Rappaport et al., *J. Clin. Pathol.* 9:261-266 (1956); Vassiliadis, et al., *J. Appl. Bacteriol.* 44:233-239 (1978)]. The broths and plates were incubated at the appropriate temperature. The plates were examined for *Salmonella* and any colonies counted. This provides the direct recovery which can be expressed as counts per gram of sample or as direct positive. When no *Salmonella* are seen from the plates relating to a sample, the corresponding Rappaport Vassiliadis broth is inoculated onto a *Salmonella* selective plate and incubated. When *Salmonella* are then seen, the result is recorded as enrichment positive, whereas when no *Salmonella* are seen the result is negative. Differences between the groups can be seen as differences in numbers of *Salmonella* isolated, numbers of direct positives, or total numbers of positives (direct plus enrichment).

The studies showed that these serovars, and *S. Infantis*, as well as other group C1 strains and serovars, did not sufficiently colonize to give a shedding profile that would consistently demonstrate reduced shedding from vaccinated birds. Further, the use of such a high challenge dose might overwhelm the level of protection obtained, thus preventing reproducible demonstration of efficacy, particularly with regard to shedding.

The efficacy of the vaccination was determined by comparison of the shedding of the challenge serovar in cloacal swabs. The shedding results are expressed as comparisons of the numbers of organisms shed as detected by direct culture and the numbers of positive cloacal swabs from the groups. Additionally, the protection against invasion to the liver and spleen was determined at post mortem examination. The results of organ isolation post mortem are expressed as a percentage of positive birds in each group either by direct culture or following enrichment (see, Table 2).

The S. Infantis challenge in these studies was not robust. Even with the high challenge dose used, shedding was too low in the control birds for meaningful results to be obtained, however it was observed in Study 3 that shedding increased at Day 7 in all groups i.e., no reduction was seen in vaccinated birds. It is thought that the high challenge doses used could break through the level of protection obtained following vaccination. Similar results have been reported by other groups using S. Infantis challenge models. Apparent differences in the effectiveness of the different formulations tested are likely to be due to variability in the challenge take between individual studies.

TABLE 2

Summary of the Results Challenge Studies

| Vaccine | Challenge | | | | | | | |
|---|---|---|---|---|---|---|---|---|
| | S. Hadar | | | | S. Infantis | | | |
| | Shedding | Caecum | Liver | Spleen | Shedding | Caecum | Liver | Spleen |
| SE/ST/SI (Study 1) | ✓ | X | ✓ | X | NR | ✓/X | NR | X |
| SE/ST/SI (Study 2) | ✓ | ✓/X | NR | ✓/X | NR | NR | ✓ | X |
| SE/ST/SH (Study 1) | ✓ | X | ✓ | ✓ | NR | ✓/X | NR | X |
| SE/ST/SH (Study 2) | ✓ | X | NR | ✓ | NR | NR | X | X |
| Quad 1 (Study 1) | ✓ | X | X | ✓ | NR | ✓ | NR | ✓ |
| Quad 1 (Study 2) | ✓/X | X | NR | ✓ | NR | NR | X | X |
| Quad 1 (Study 3) | ✓ | X | NR | ✓ | NR* | X | ✓/X | X |
| Quad 2 (Study 3) | ✓ | X | NR | ✓ | NR* | X | ✓ | X |
| Quad 3 (Study 3) | ✓ | X | NR | ✓ | NR* | X | ✓ | X |

✓—protection shown by reduction in counts or number of positives.
X—indicates no protection seen, i.e., no reduction in counts or number of positives.
NR—No result. The counts or number of positives in the controls were too low.
NR*—same shedding pattern in all groups, see below.
✓/X—An equivocal result.

Results

The results for the isolations from cloacal swabs are shown in FIGS. 1A-1C as individual points for each bird and denote the $\log_{in}$ cfu/g of the challenge serovar. The mean counts from each group are shown linked by a solid line for clarity. The results of the post mortem sample isolations in FIGS. 2A-2B and FIGS. 3A-3C are expressed as the percentage of samples which were positive for isolation of the challenge. In Study 1, samples were taken post mortem from some birds in each group at Day 7 and the remainder on Day 14 post challenge.

Efficacy Against Shedding Following an S. Hadar Challenge:

Study 1:

FIG. 1A shows between Day 3 and Day 5 post challenge with S. Hadar the shedding from the control birds was maintained at about 3 $\log_{10}$, and on Day 5 all birds were positive by direct culture. For all of the vaccinated groups, SE/ST/SI, SE/ST/SH, and Quad 1 (see Table 1 above), including the trivalent vaccine formulated with S. Infantis (SE/ST/SI), the mean shedding reduced over the period and the numbers of birds negative by direct culture increased. The homologous vaccine (SE/ST/SH) had the sharpest decline, whereas the quadravalent vaccine (Quad 1) had the highest number of negative birds.

Study 2:

Study 2, was a repeat of Study 1 above, except as depicted in FIG. 1B, data is included for Day 7 post challenge with S. Hadar. As can be seen in FIG. 1B, the mean shedding was again around 3 $\log_{10}$, but there were a number of birds in the control group that did not shed the challenge as detected by direct culture and consequently, the mean shedding of the vaccinated groups was in some cases higher than the control group. The effect of vaccination is however confirmed by the rapid decrease in mean shedding (the counts being at least 10-fold lower than in the control group by Day 7) and the increasing numbers of negative birds in each of the trivalent vaccine groups. The quadravalent vaccine, Quad 1, did not perform as well in Study 2 as it had in Study 1.

Study 3:

As depicted in FIG. 1C all three quadravalent vaccine groups, i.e., Quad 1, Quad 2, and Quad 3 (see, Table 1 above) had counts approximately 10-fold lower than the control group by Day 7. This included the group vaccinated with Quad 3, which was the formulation having the 50% antigen dose. The two groups vaccinated with the vaccines containing 25% adjuvant, i.e., Quad 2 and Quad 3, also showed lower counts on Day 3 and Day 5 than the group vaccinated with the vaccine containing the 40% adjuvant, i.e., Quad 1.

Isolations Post Mortem Following an S. Hadar Challenge:

In Study 1, on Day 7, the caecal contents from the majority of birds in all groups were positive (see, FIG. 2A). In the liver, each trivalent vaccine reduced invasion to the extent where no samples were directly positive. The reduction in the proportion of spleen samples, which were directly positive, appears to show a serovar-specific effect, where only the trivalent vaccine containing S. Hadar cells and the quadravalent vaccine showed a reduction. There were few positive samples from any liver or spleen samples taken on Day 14 post challenge.

The results of Study 2 show that the trivalent SE/ST/SI vaccine group had reduced numbers of positive caecal content samples compared to the other groups (see, FIG. 2B). The pattern of isolations from the spleen were similar to Study 1, although the proportion of positive controls was higher, and all vaccines showed a reduction in the proportion of positive samples. There were too few positive samples from the livers from the control birds in this study for a valid analysis.

In Study 3, while the caecal contents samples from all birds were positive, few liver samples were positive (5 of 15 controls compared to 1 or 2 of 12 vaccinated birds). Each vaccine showed a level of protection from spleen colonization with the vaccines containing 25% adjuvant having the lowest proportions of positives as shown in the Table 3 below.

TABLE 3

Percentage of Positive Spleen Samples

| | Vaccine dose/adjuvant | | | |
|---|---|---|---|---|
| | Full/40% | Full/25% | Half/25% | Control |
| Percentage positive | 58 | 33* | 31* | 87 |

*Significantly different to controls p = <0.05

Efficacy Against Shedding Following an *S. Infantis* Challenge:

In Studies 1 and 2 there was no clear indication that *S. Infantis* colonized the caecum in the control birds. By seven days post challenge there were no birds positive by direct culture. In Study 3 the differences in mean counts between the groups on each day was low, although quadravalent vaccines 1 and 2 had fewer birds positive on direct culture on Day 3 post challenge compared with both the controls and Quad 3, see, Table 4 below. The counts increased markedly from Day 5 to Day 7 in each group indicating that the challenge dose was high enough to break through the protection.

TABLE 4

Percentage of Direct Positive Birds on Day 3 Post Challenge

| | Vaccine dose/adjuvant | | | |
|---|---|---|---|---|
| | Full/40% | Full/25% | Half/25% | Control |
| Percentage positive | 8.3 | 0 | 33 | 42.8 |

Isolations Post Mortem Following an *S. Infantis* Challenge:

In Study 1 at Day 7 post challenge with *S. Infantis* there were fewer positive caecal content samples in any of the vaccinated groups compared to the controls, but the proportions of positive liver and spleens from the controls were too low for a meaningful analysis to be made (see, FIG. 3A). The spleen sample data from Day 14 post challenge showed a reduction in the proportion of samples positive from the quadravalent group (Quad 1) compared with the controls (see, FIG. 3B).

In Study 2 at Day 7, there were too few positive samples from the caecum for a valid analysis. No reduction in the proportion of positive spleen samples was observed with any of the formulations (see, FIG. 3C). Homologous protection from invasion of the liver was however observed as there were fewer direct positive samples from both the trivalent SE/ST/SI and the quadravalent vaccine (Quad 1; see, FIG. 3C).

TABLE 5

Percentage of Positive Liver Samples at Post Mortem

| | Vaccine dose/adjuvant | | | |
|---|---|---|---|---|
| | Full/40% | Full/25% | Half/25% | Control |
| Percentage positive | 58 | 36 | 40 | 71 |

In Study 3, at examination post mortem on Day 7 no protective effect with respect to reductions in the proportion of positive caecal or spleen samples was observed for any of the formulations. Each vaccine however showed a level of protection from liver invasion with the vaccines containing 25% adjuvant (Quad 2 and Quad 3) having the lowest proportions of positives as shown in the Table 5 above.

Example 2

Passive Protection in Broiler Chicks Challenged with *S. Hadar* or *S. Infantis* at 4 Days of Age Parent birds were vaccinated with an *S. Enteritidis*+*S. Typhimurium*+*S. Infantis* (SE/ST/SI) combination vaccine with 25% Rehydrogel™, or alternatively left unvaccinated as controls. Broiler chicks at four days of age that had hatched from eggs of the vaccinated or unvaccinated hens, were challenged with either *S. Hadar* or *S. Infantis* to test for passive protection against these two distinct serovars.

The recovery of the challenge serovars from the study birds was high. No differences were seen between the vaccinated and control groups for shedding of challenge by cloaca swab monitoring, or in caecal contents at post mortem. However, there were fewer positive birds in the vaccinated groups than the control groups when invasion to both liver and spleen were considered. This was found most consistently at the 10 days post challenge sampling and when a challenge of $10^2$ cfu of *S. Hadar* or $10^3$ cfu of *S. Infantis* was used. Both the *S. Hadar* and *S. Infantis* challenge groups showed very similar results for protection against organ invasion despite the fact that the parent flock received a vaccine that comprised *S. Infantis*, but not *S. Hadar*. These results are consistent with those of Example 1 above, and therefore, they provide strong evidence of cross protection between these two distinct *Salmonella enterica* sub-groups.

Experimental Methods

Eggs from parent flocks that either had been vaccinated with an *S. Enteritidis*, *S. Typhimurium*, and *S. Infantis* (SE/ST/SI) combination vaccine, or alternatively, had not been vaccinated were stored, hatched and incubated separately to ensure that origin of the hatched chicks could be identified. At one day of age the chicks were allocated to four groups of 15 from vaccinated birds and four from unvaccinated birds, with each group contained separately. The birds were challenged at 4 days of age with the appropriate *Salmonella* strain and dose according to group allocation (see, Table 6 below).

TABLE 6

Experimental Protocol for Passive Protection Challenge

| Group | Birds (No.) | Vaccination | Challenge Strain | Dose (per 0.5 ml) |
|---|---|---|---|---|
| 1 | 15 | SE/ST/SI | *S. Hadar* | $10^2$ cfu |
| 2 | 15 | Control | *S. Hadar* | |
| 3 | 15 | SE/ST/SI | *S. Hadar* | $10^4$ cfu |
| 4 | 15 | Control | *S. Hadar* | |
| 5 | 15 | SE/ST/SI | *S. Infantis* | $10^3$ cfu |
| 6 | 15 | Control | *S. Infantis* | |
| 7 | 15 | SE/ST/SI | *S. Infantis* | $10^5$ cfu |
| 8 | 15 | Control | *S. Infantis* | |

The course of the infection was monitored by cloacal swab examination of the birds at 3, 5, 7, and 10 days post challenge. The presence of the challenge organisms in cloacal and caecal contents and dissemination to liver and spleen samples was determined by post mortem examination of half the birds in each group at 7 days post challenge and the remainder at 10 days post challenge.

Results

Post Challenge with *S. Hadar*:

No reduction in shedding or difference in caecal isolations from vaccinates compared to controls was seen with either challenge dose.

At days 7 and 10 post challenge at the higher challenge level ($10^4$ cfu/dose) there was a reduction seen in isolations from the liver and spleen on day 7 and day 10, and for the lower challenge level ($10^2$ cfu/dose) a reduction was seen comparing vaccinates to controls for both liver and spleen at day 10 post challenge. The proportion of positive birds reflects the numbers isolated with vaccinated groups having fewer positive samples at day 7 and day 10, following a lower dose challenge. The low dose challenge only showed a protective effect of vaccination at day 10 post challenge. However, this was the greatest difference between the vaccinated and control birds and reflected an increasing proportion of positive control birds against a reducing proportion of positive vaccinated group birds. Results are tabulated as a total percentage of birds positive following the *S. Hadar* challenge in Table 7 below.

TABLE 7

Total Percentage of Birds Positive following an *S. Hadar* Challenge (Direct and Enrichment Culture at Days 7 and 10)

| Group | Vaccination | Challenge Strain | Caecal | Liver | Spleen |
|---|---|---|---|---|---|
| | | | % Total Positive, Day 7 | | |
| 1 | SE/ST/SI | $10^2$ *S. Hadar* | 100% | 38% | 25% |
| 2 | Control | $10^2$ *S. Hadar* | 100% | 0% | 0% |
| 3 | SE/ST/SI | $10^4$ *S. Hadar* | 100% | 25% | 50% |
| 4 | Control | $10^4$ *S. Hadar* | 100% | 63% | 75% |
| | | | % Total Positive, Day 10 | | |
| 1 | SE/ST/SI | $10^2$ *S. Hadar* | 100% | 17% | 33% |
| 2 | Control | $10^2$ *S. Hadar* | 100% | 71% | 71% |
| 3 | SE/ST/SI | $10^4$ *S. Hadar* | 100% | 14% | 57% |
| 4 | Control | $10^4$ *S. Hadar* | 100% | 57% | 86% |

Post Challenge with *S. Infantis*:

The challenge with *S. Infantis* at $10^3$ cfu initially showed a reduction in shedding from the vaccinated group on day 3, however this difference between groups was reduced on later sampling days. The higher dose challenge level ($10^5$ cfu/dose) showed no reduction in shedding for vaccinate groups across all time points. Almost all caecal samples were positive.

The isolations of *S. Infantis* from liver and spleen resulted in fewer positive samples from vaccinated than control groups at day 7 post challenge with the higher challenge dose, while both challenge levels showed a protective effect of vaccination at day 10 (see, Table 8 below). With the lower challenge dose there was a reducing proportion of positive birds between 7 and 10 days compared to an increasing proportion of positive control birds.

TABLE 8

Total Percentage of Birds Positive following an *S. Infantis* Challenge (Direct and Enrichment Culture)

| Group | Vaccination | Challenge Strain | Caecal | Liver | Spleen |
|---|---|---|---|---|---|
| | | | % Total Positive, Day 7 | | |
| 5 | SE/ST/SI | $10^3$ *S. Infantis* | 100% | 50% | 75% |
| 6 | Control | $10^3$ *S. Infantis* | 100% | 38% | 25% |
| 7 | SE/ST/SI | $10^5$ *S. Infantis* | 100% | 50% | 50% |
| 8 | Control | $10^5$ *S. Infantis* | 100% | 88% | 88% |
| | | | % Total Positive, Day 10 | | |
| 5 | SE/ST/SI | $10^3$ *S. Infantis* | 100% | 14% | 43% |
| 6 | Control | $10^3$ *S. Infantis* | 100% | 71% | 86% |
| 7 | SE/ST/SI | $10^5$ *S. Infantis* | 100% | 29% | 57% |
| 8 | Control | $10^5$ *S. Infantis* | 86% | 57% | 71% |

Conclusions

The vaccine groups at both *S. Hadar* challenge levels showed no reductions compared to the controls in the cloacal shedding (numbers shed and numbers of positive samples) or caecal content samples. However, the vaccine groups at both challenge levels showed reductions in organ colonization with maximum differences seen in the lower challenge level ($10^2$ cfu) at day 10 post challenge. Therefore, evidence of cross protection against an *S. Hadar* challenge was observed in chicks that had been passively immunized against *S. Infantis*, in terms of reducing organ colonization.

The vaccine groups at both *Salmonella Infantis* challenge levels showed little reduction compared to the controls in the cloacal shedding or caecal content samples. A reduction in organ invasion was seen with the vaccinated groups showing fewer positive organ samples than the controls with a similar pattern as seen with the *S. Hadar* challenge.

Example 3

Efficacy Testing of a Trivalent Vaccine Against *S. Hadar* Challenge in Layers at 14 Weeks of Age Summary Six week old SPF origin layer type chickens were immunised with a trivalent vaccine containing equal numbers of *S. Enteritidis*, *S. Typhimurium*, and *S. Infantis* formalin killed cells which had been grown under iron restricted conditions. A second dose of vaccine was given at 10 weeks of age. Four weeks following the second vaccination the birds and an unvaccinated cohort were challenged by the oral route with *S. Hadar*, and shedding of the challenge strain was monitored by cloacal swab examination. Dissemination of challenge bacteria to internal organs was determined by post mortem examination of birds at 10 and 14 days post challenge.

There were significantly fewer challenge organisms shed from the vaccinated group when the level of individual bird shedding was compared to the control group ($p=0.001$). The proportion of positive spleen samples from control birds was significantly higher than the vaccinated group ($p=0.01$). There was no recovery of the challenge organism from liver culture in this study.

The trivalent vaccine tested here has shown efficacy against *S. Hadar* challenge in that:

The number of *S. enterica* serovar *Hadar* in fresh faeces samples from vaccinated chickens after challenge at the different days of sampling was lower in vaccinated than in control birds for each time-point sampled; when total shedding over time was compared the number of organisms shed by vaccinated birds was significantly lower than by the control birds.

The total number of positive spleen samples showed a significant reduction in vaccinated birds when compared to controls.

Experimental Design

Layer birds of SPF origin were reared as one group in conventional chicken accommodation for several weeks in order to develop a common normal intestinal flora, until the challenge phase of the study. 55 birds were vaccinated at 6 weeks of age with 0.5 ml of vaccine given intramuscularly in the breast. Four weeks later a second dose of vaccine was given by the same route. 52 birds remained unvaccinated as a control group. Prior to the time of challenge administration the birds were transferred to containment facilities to be housed in their separate groups in floor pens.

The birds were exposed to oral challenge infection at approximately 14 weeks of age with an *S. Hadar* challenge. Food was withdrawn from the birds on the day prior to challenge and then re-introduced after challenge. The course of the infection was monitored by cloacal swab examination of the same 30 birds of each group at 3, 5, 7, 10, and 14 days following challenge. The presence of the challenge bacterium in liver and spleen samples was determined by examination of samples taken at post mortem from the birds not selected for cloacal sampling either on day 10 post challenge, or for the remaining birds at 14 days post challenge. Study groups were as presented in Table 9.

TABLE 9

Study Groups:

| Group | No of birds | Vaccine | Target Challenge dose in 20 ml |
|---|---|---|---|
| 1 | 55 | Batch 29 | $10^8$ cfu/bird |
| 2 | 52 | None | |

Vaccine:

The vaccine contained $1.5 \times 10^9$ cells of iron restricted, formalin killed cells of each of *S. Typhimurium*, *S. Enteritidis* and *S. Infantis* and an aluminium hydroxide adjuvant. The vaccine had passed a sterility test and analytical tests before use.

Challenge:

The birds were each challenged with $3.8 \times 10^8$ c.f.u. of *S. Hadar*, strain PT16, freshly prepared from an overnight culture at 37° C. in a micro-aerophilic environment.

The cultures were concentrated 10-fold by centrifugation, and checked for viability and purity by plating onto Blood Agar. The challenge was administered as a 20 ml oral dose per bird.

Animals:

SPF White Leghorn Layers, of mixed sex, 6 weeks old at the time of first vaccination.

Methods and Procedures

Environmental sample testing: Samples of the litter were tested for the presence of *Salmonella* at the time of vaccination and challenge by collecting samples of faecal material from at least five separate places from the floor of the pen into a sterile container. The faecal material was suspended in Buffered Peptone Water to faeces to medium ratio of 1:10 w/v and incubated at 37° C. for up to 24 hours. A 100 μl sample of the growth from the broth was inoculated into 10 ml volumes of Rappaport Vassiliadis (RV) broth and incubated for up to 72 hours at 42° C. A loopful of each RV broth growth was inoculated onto a Brilliance™ *Salmonella* Selective media (Oxoid), and incubated for up 24 hours at 37° C. The presence of any *Salmonella* was shown by the presence of mauve colonies. Any suspect colonies were confirmed by serological identification. The isolation of *Salmonella* from the environment would have invalidated the study.

Serology:

Blood samples were taken from the radial vein of each study bird prior to challenge. The serum samples were tested for the presence of antibodies to *S. Typhimurium, S. Enteritidis* and *S. Infantis* using an in-house ELISA. The assay involved the incubation of dilutions of test and reference sera on microtitre plates previously coated with flagellae prepared from *Salmonella* cells of the relevant serovar. Following washing, the bound antibodies were detected using an anti-chicken IgY antibody conjugated to peroxidase, followed by incubation with a substrate. The colour development was stopped with acid and the optical densities read at 450 nm. Antibody levels were calculated relative to the reference serum for each serovar.

*Salmonella* Isolations

Cloacal swabs and post-mortem samples of liver and spleen were examined for the presence of the challenge bacterium as described in Example 1.

Analysis of Data:

The number of *Salmonella* isolated per gram of faeces from cloacal swabs were calculated from isolations from direct culture. The numbers of positive samples from each group following enrichment was also recorded.

The geometric means of shedding, totals of positive samples and total shedding per bird were calculated. The total shedding of each bird in the groups over the study duration was calculated using an 'area under the curve' estimation and the two groups were compared using a two sample t test.

The proportions of birds having positive spleen samples (by both direct and enrichment culture) were compared using contingency tables (Chi square analysis with Yates continuity correction) where applicable. The results for liver samples were not included as no liver samples were found to be positive for *Salmonella*.

Results

Figure 4:
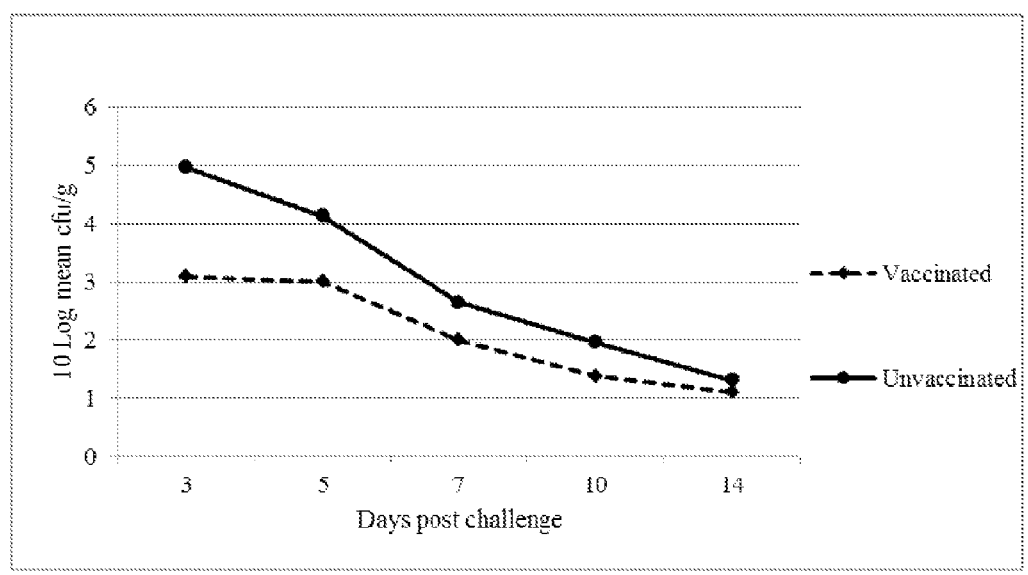

Shedding of *Salmonella Hadar* Challenge Strain—Cloacal Swab Results:

The geometric mean numbers of *Salmonella* recovered at each time point from cloacal swabs after challenge were calculated. The $\log_{10}$ of the count per gram of caecal content was calculated, and the mean calculated for each group at each time point (see FIG. 4 and Table 10).

At every time point until 14 days post challenge there were higher mean levels of recovery from the control group compared to the vaccinated group. At day 14 post challenge the numbers shed by both groups were similar. The total shedding over time for each bird was calculated and there was shown to be a statistically significant difference between the vaccinated group (1) and the control group (2) (p=0.001), when compared by t test.

TABLE 10

Comparison of geometric mean log10 cfu/g recovered from vaccinated and control birds over time.

| | Mean $Log_{10}$ cfu/g | |
|---|---|---|
| Days Post Challenge | Vaccinates (Group 1) | Controls (Group 2) |
| Day 3 | 3.09 | 4.97 |
| Day 5 | 3.00 | 4.13 |
| Day 7 | 2.00 | 2.65 |
| Day 10 | 1.38 | 1.96 |
| Day 14 | 1.10 | 1.31 |

Isolation of *S. Hadar* Post Mortem:

At each time point there were more positive samples from the unvaccinated birds, both from direct culture and as a total, than from the vaccinated group.

At 10 days post challenge a total of 9 of 25 (36%) spleen samples from the vaccinated group were positive, 7 of them direct, compared to 16 of 22 (73%) from the control group, of which 11 were direct.

Figure 2:
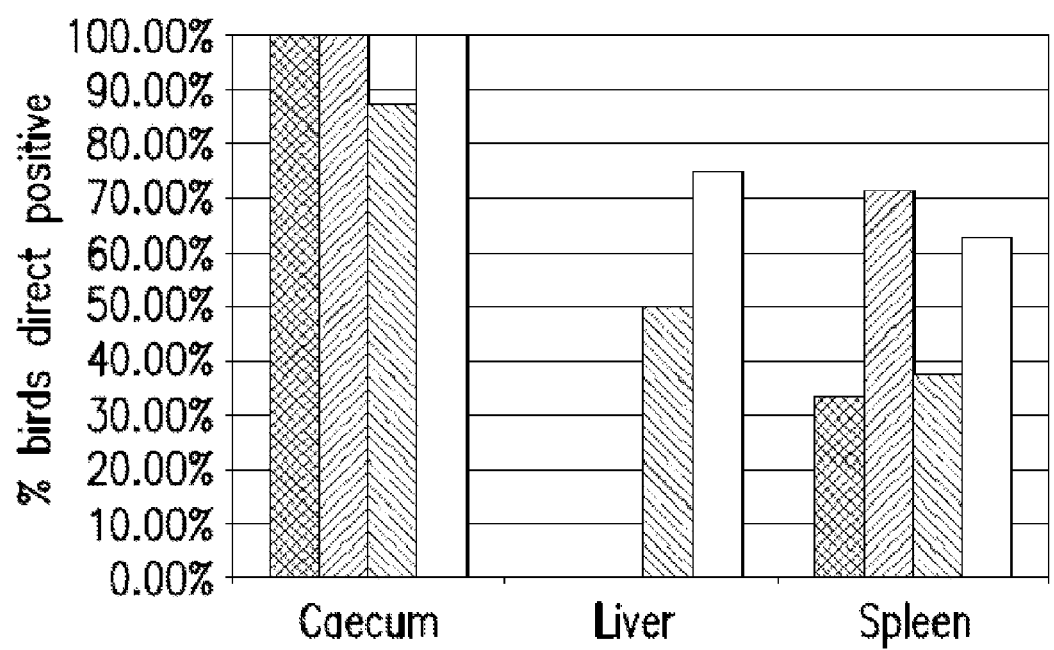
Figure 2:
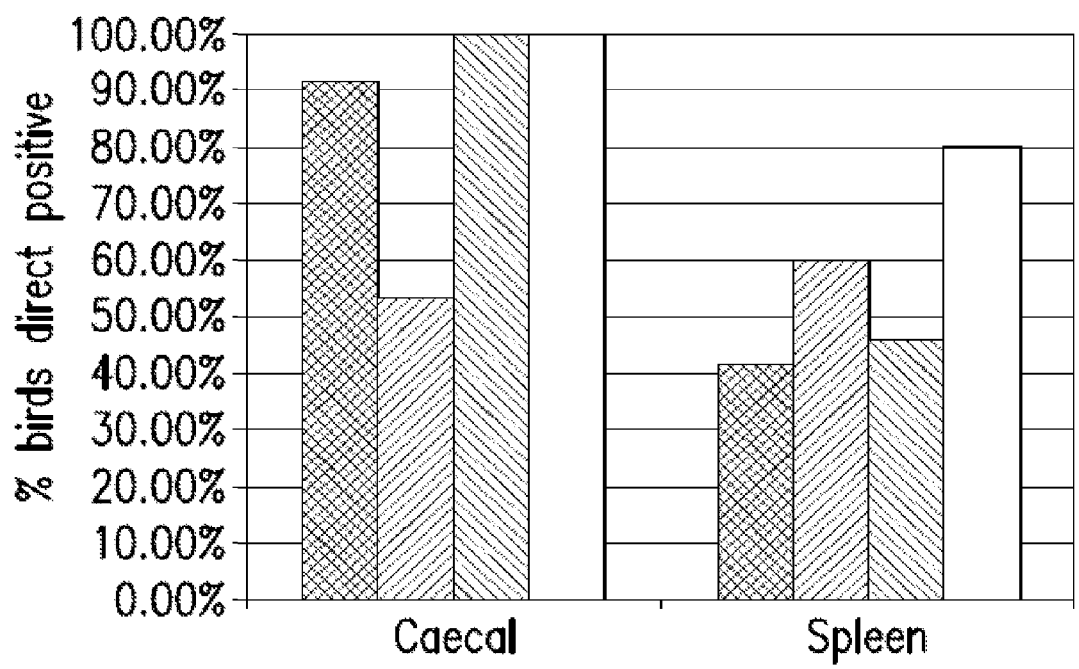
Figure 3:
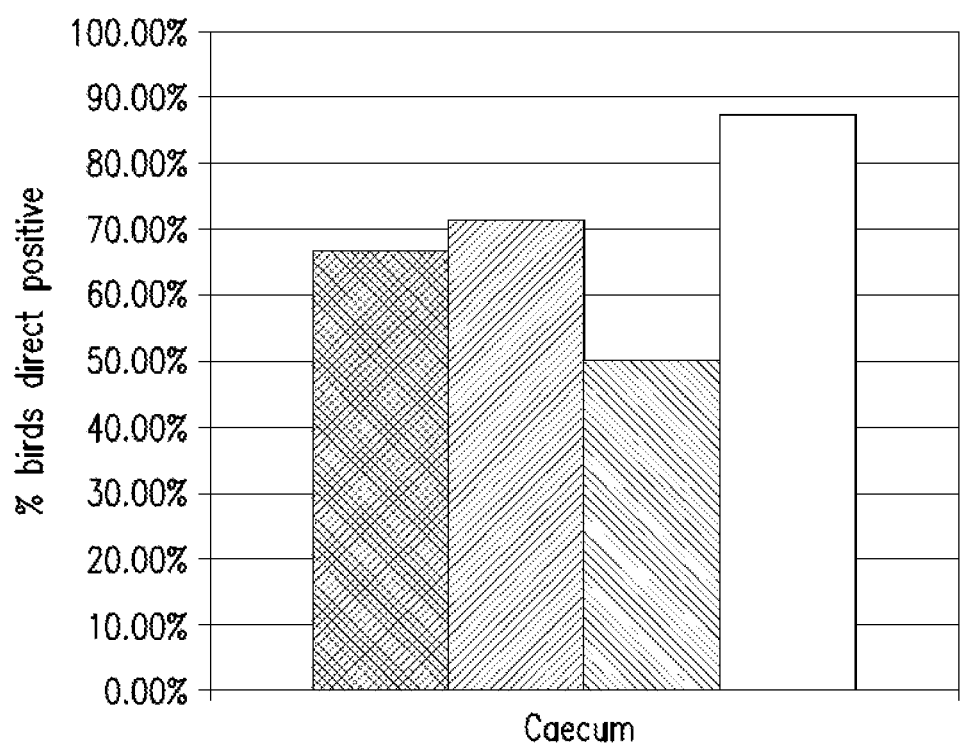
Figure 3:
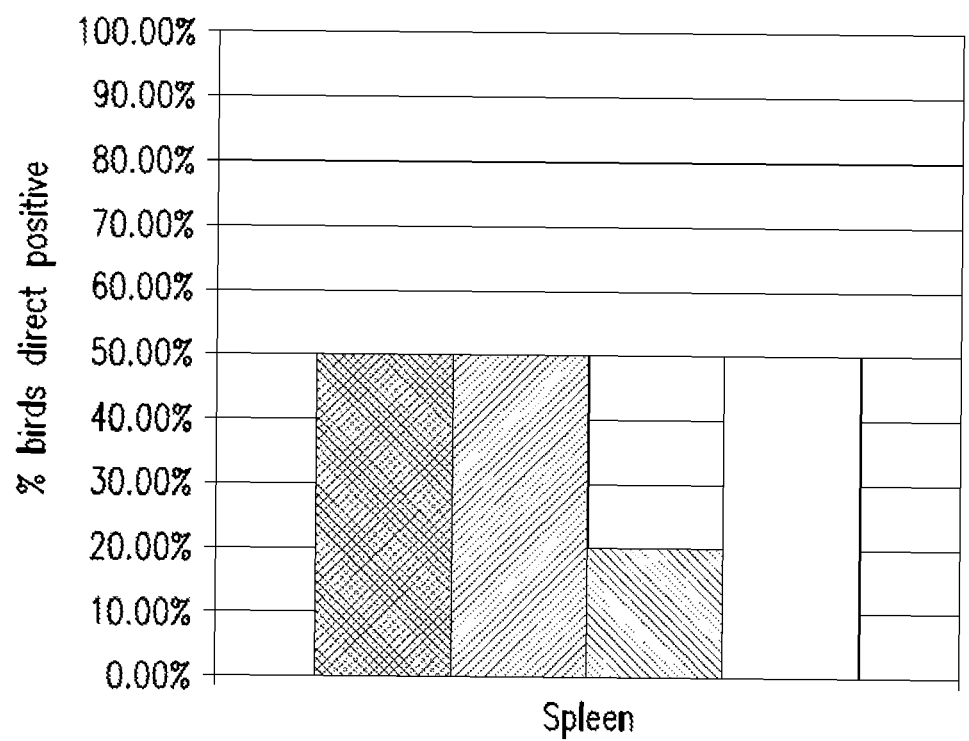
Figure 3:
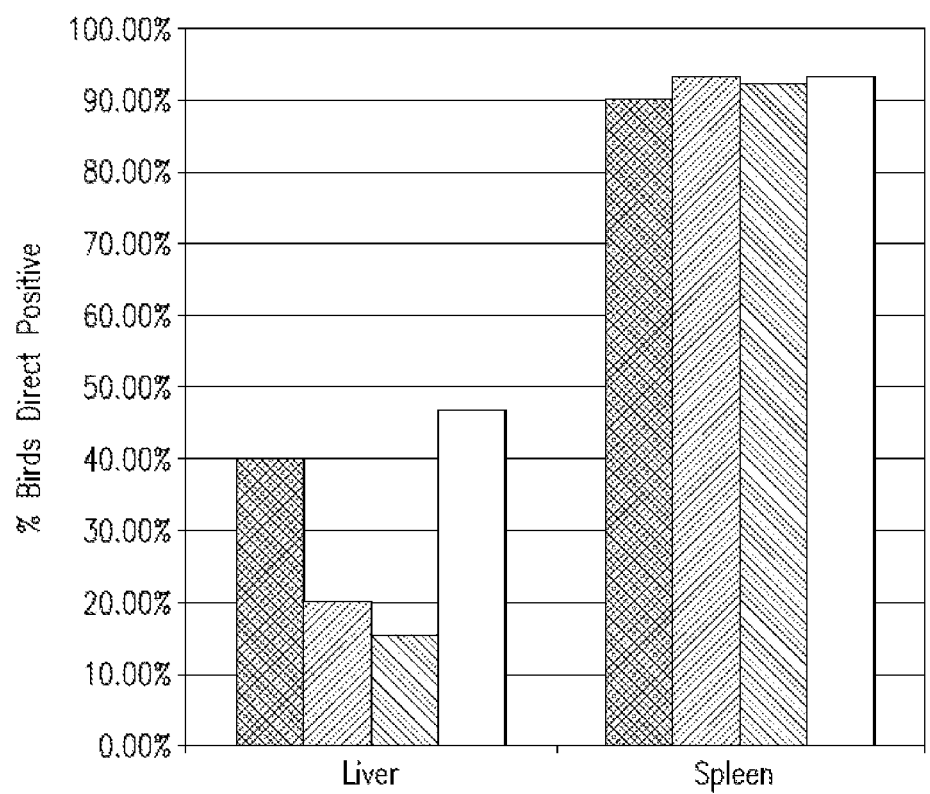

At 14 days post challenge a total of 8 of 30 (27%) samples from the vaccinated group were positive, 4 of them direct, compared to 14 of 30 (47%) cultures from the control group of which 11 were direct (see FIG. 2 and Table 11).

TABLE 11

Number of Positive Spleen Samples (direct and enrichment culture).

| | Positive | Negative | Total |
|---|---|---|---|
| Spleen Day 10 post-challenge | | | |
| Group 1 - Vaccinates | 9 | 16 | 25 |
| Group 2 - Controls | 16 | 6 | 22 |
| Spleen Day 14 post-challenge | | | |
| Group 1 - Vaccinates | 8 | 22 | 30 |
| Group 3 - Controls | 14 | 16 | 30 |

Figure 5:
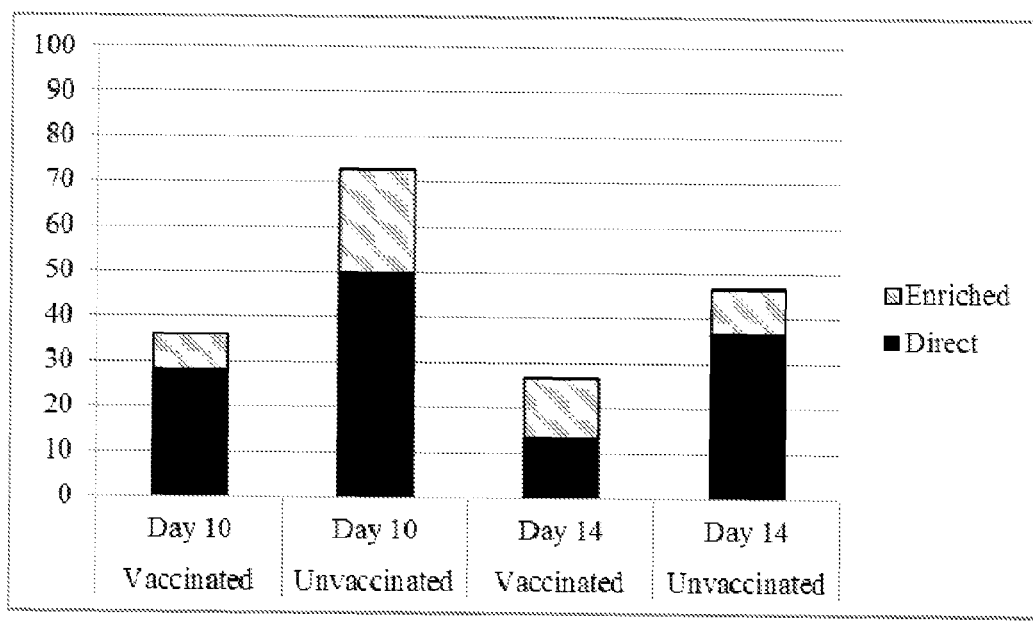

There was no recovery of challenge organism by direct or enrichment culture from liver samples taken at both 10 and 14 days post challenge See FIG. 5 for the percentage of total positive spleen samples (direct and enrichment culture) from groups 1 and 2, at 10 and 14 days post challenge.

The numbers of birds yielding a positive sample post mortem are summarized in Table 12.

TABLE 12

Summary of the Total Number of Positive Birds at Post Mortem (Direct and Enrichment Culture).

| | Positive | Negative | Total Number of Birds Sampled |
|---|---|---|---|
| Group 1 - Vaccinates | 17 | 28 | 55 |
| Group 2 - Controls | 30 | 22 | 52 |

Chi square value (Yates' corr.) = 6.736 (p = <0.01)

Conclusions

The aim of this study was to demonstrate the efficacy of a trivalent *Salmonella* vaccine against a heterologous *S. Hadar* challenge infection.

The efficacy of the vaccine in reducing shedding was convincingly shown as there were significantly fewer challenge organisms shed in faeces from the vaccinated group compared to the control group over the duration of the study (p=0.001); starting off at a 100 fold lower level of shedding.

Impressive efficacy against dissemination to internal organs was also shown as there were significantly fewer birds from the vaccinated group presenting positive samples at post mortem compared to the controls (p<0.01); in fact dissemination levels were effectively halved.

Consequently, the trivalent vaccine tested here resulted in a significant reduction of the number of *S. Enterica* in fresh faeces samples from vaccinated chickens as compared to controls, which remained lower until the end of the test. Also, the number of *Salmonella* positive samples from liver or spleen was significantly lower in vaccinates than in controls.

The invention claimed is:

1. A trivalent *Salmonella* vaccine comprising a liquid suspension of formalin-killed, iron-restricted *Salmonella enterica* serogroup C1 *Infantis* serovar cells, *Salmonella enterica* serogroup D *Enteritidis* serovar cells, and *Salmonella enterica* serogroup B *Typhimurium* serovar cells, and an aluminium hydroxide adjuvant; wherein said serogroup C1 serovar cells, said serogroup D serovar cells, and said serogroup B serovar cells all had been grown in an iron-restricted medium that comprised an iron chelator; and wherein when administered to a flock of poultry said trivalent *Salmonella* vaccine provides protection against a disorder arising from a *Salmonella enterica* serogroup C2-3 infection.

2. The trivalent *Salmonella* vaccine of claim 1, that further includes one or more strains of avian rhinotracheitis, infectious bronchitis virus, Newcastle disease virus, and egg drop syndrome virus.

* * * * *